United States Patent [19]

Curry

[11] Patent Number: 5,153,899
[45] Date of Patent: Oct. 6, 1992

[54] PORTABLE TIRE X-RAY APPARATUS AND METHOD
[76] Inventor: Leonard O. Curry, 8363 Nieman Rd., Lenexa, Kans. 66214
[21] Appl. No.: 726,928
[22] Filed: Jul. 8, 1991
[51] Int. Cl.$^5$ .............................................. G01B 15/06
[52] U.S. Cl. .......................................... 378/61; 378/58
[58] Field of Search ............................................ 378/61
[56] References Cited
U.S. PATENT DOCUMENTS
3,826,919  7/1974  Yaroshub et al. ..................... 378/61

Primary Examiner—Craig E. Church
Attorney, Agent, or Firm—Litman, McMahon & Brown

[57] ABSTRACT

A portable tire x-ray apparatus includes a frame having motor driven rollers that support a tire vertically and cause the tire to rotate about a central axis thereof. A pair of pneumatically actuated spreader fingers spread the sidewalls of the tire as the tire is being rotated. An x-ray source and an x-ray image intensifier are mounted at either end of an arm and are spaced apart a distance which allows the x-ray source to irradiate selected sectors of the tire to create a fluoroscopic image of the selected sector on the x-ray image intensifier. The arm is connected to a support which is, in turn, connected to a motor drive and is pivotable to three preselected different positions. In one of the positions, one sidewall of the tire is examined, in the second position, the tread is examined, and in the third position, the opposite sidewall is examined. A video camera is optically coupled to the x-ray image intensifier and is connected to a VCR and a live monitor to convert the fluoroscopic image on the x-ray image intensifier to a video signal for display and recording. The VCR is also provided with a monitor so that recorded images of the tire can be played back simultaneously with live images for comparison. The tire rotation motor, the x-ray/image intensifier pivoting motor, the x-ray source, the x-ray image intensifier, and the video camera are remotely controllable from the safety of an x-ray protected compartment.

5 Claims, 3 Drawing Sheets

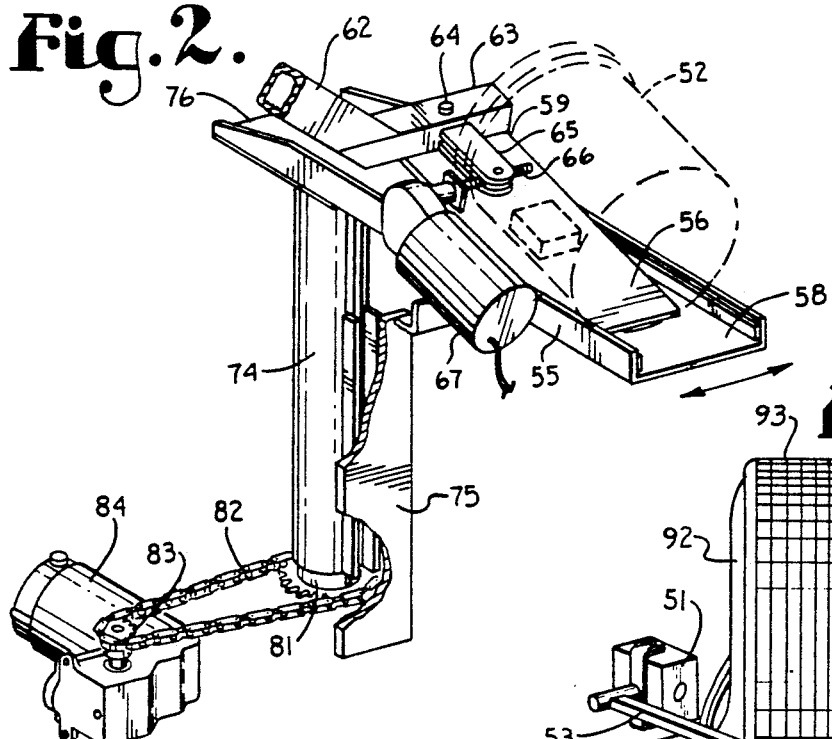
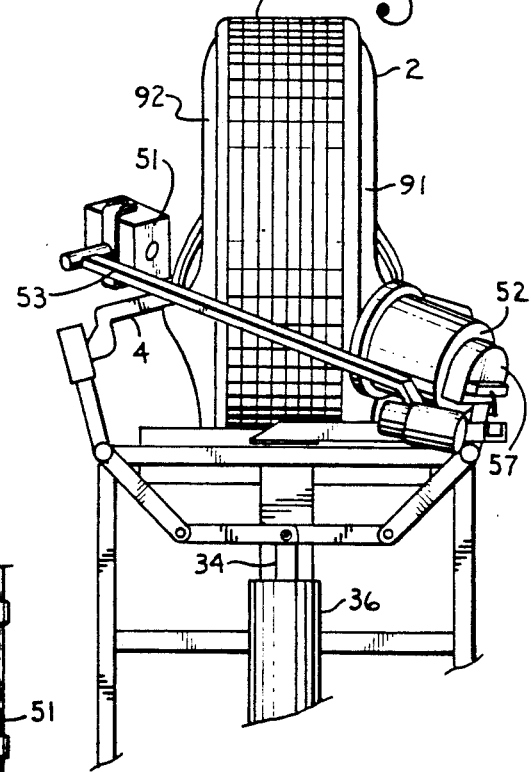
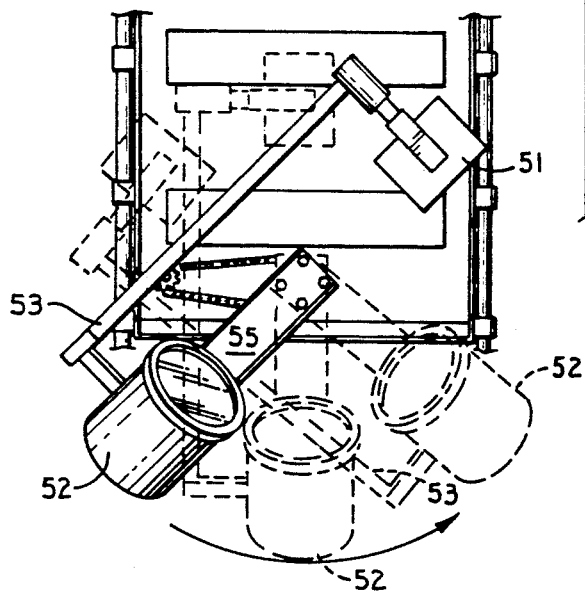
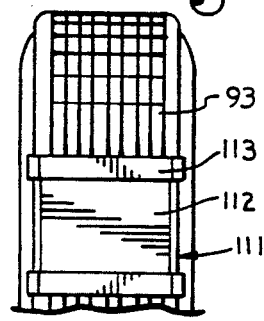

PORTABLE TIRE X-RAY APPARATUS AND METHOD

BACKGROUND OF THE INVENTION

The present invention relates to a tire inspection apparatus and methods to such apparatus which are particularly suited to the tire retreading industry.

Various types of x-ray equipment have been used in the past for the inspection of tires to discover defects not visible by the naked eye. For the most part, such apparatus have been associated with automotive servicing or the maintenance of tires. Apparatus installed in service stations and tire retailers are usually adapted for inspection of tires which are mounted on rims for the discovery and location of defects incurred in the use of the tires on the road so that the defects can be repaired or the tire replaced before a blowout endangers life. In the tire manufacturing business, tire makers universally use x-ray apparatus for quality control purposes to discover manufacturing defects.

In trucking operations involving medium and large trucks, it is a standard practice to recap or retread tires after a period of use in which the original tread has worn away. The reason for this is simple: the cores of medium and large truck tires are relatively expensive. In most cases, little damage of a non-repairable nature occurs to the core (referred to as a coram once the tread is worn away) of truck tires in normal use such that the tires can be safely retreaded if substantially undamaged tire carcasses are reused. On the other hand, when a carcass with structural defects is retreaded, the tire can be completely destroyed under the pressures and temperatures which occur during normal use. Such failures can create hazards to the driver and others on the road, as well as causing expensive down time for the truck and cargo. Visual inspection does not always indicate if a tire carcass has been damaged. While large punctures and damage to the rubber portions of a tire can often be found by visual inspection, small punctures and damage, especially to the tire cords or belts are not usually visible externally.

The hazards to humans from overexposure to penetrating radiation, such as x-rays, are more fully appreciated in current times than in the past. Thus, while various types of x-ray apparatus for general and specialized tire servicing establishments have been proposed, such apparatus is not in general use at this time because of the need to provide specialized training to infrequent operators of such equipment, the expense of purchasing and maintaining such equipment, and the potential liabilities involved. In contrast, quality control and product liability concerns in tire manufacturing require that newly manufactured tires be closely inspected. Since x-ray inspection of tires in such manufacturing settings is an ongoing operation, the expense of x-ray equipment and the training of personnel can be more easily justified. As a result, the development and availability of industrial tire x-ray equipment has continued while the development and availability of similar equipment suitable for small commercial operators has lagged.

For safety reasons, it is necessary to inspect both sidewalls and the tread of a tire. Conventionally, testing equipment has either included multiple x-ray sources and image intensifiers to simultaneously x-ray both sidewalls and the tread of a tire, or the tire has been physically removed from the inspection equipment and reversed, which is time consuming and labor intensive.

Applicant has addressed certain of the concerns of the industry in his previous U.S. Pat. Nos. 4,839,914 and 4,977,586 which are incorporated herein by reference. However, certain problems were not fully resolved by the devices disclosed in the two prior patents.

In particular, U.S. Pat. No. 4,839,914 is directed to a portable tire x-ray inspection device which has a single x-ray source and image intensifier which is mounted in a fixed position with respect to a tire being inspected. The tire is mounted on a platform which has a plurality of rollers which rotate the tire and permit one entire sidewall to be examined without physically moving the x-ray apparatus. While this arrangement was an improvement, it did not solve the problem of the operator having to physically remove and reverse the tire in order to inspect the opposite sidewall.

U.S. Pat. No. 4,977,586 was an improved portable x-ray inspection apparatus which mounts the x-ray source and the image intensifier on a wheeled carriage which permits it to be rotated around the tire so that both sidewalls of the tire can be inspected without physically removing the tire from the apparatus. This arrangement has proven to be satisfactory except that the x-ray apparatus and image intensifier must be physically swung around the tire which means that the operator must leave his shielded environment both to mount the tire for inspection of a first sidewall and again to swing the x-ray apparatus about the tire to inspect the opposite sidewall.

Another problem which is not addressed by the above-cited patents is that a tire can be much more reliably inspected if the tire sidewalls are spread apart during inspection. A normal truck tire in an unspread condition will have the radially inner edges of the sidewalls spaced closely together, for example, approximately 2"-4". This relatively small spacing does not leave enough space to position an x-ray source relative to the tire without some distortion. This means that x-rays must penetrate a portion of the near sidewall and then the subject opposite sidewall before reaching the image intensifier. This decreases the quality and reliability of the resulting analysis and can even cause invalid results if a defect is located near the edge of the near sidewall, but is attributed to the subject opposite sidewall. Furthermore, the tread cannot be reliably inspected if the x-ray source cannot be inserted in between the sidewalls.

It is clear, then, that a need exists for a portable tire x-ray apparatus which can spread the sidewalls while rotating a tire to be inspected and which can automatically swing the x-ray source and image intensifier relative to the tire so that an operator can inspect a tire without leaving a shielded environment, thereby also reducing the time required to inspect each tire.

SUMMARY OF THE INVENTION

The present invention provides an apparatus and method for x-ray tire inspection which are particularly well adapted for inspecting tires prior to tire retreading operations. The apparatus includes a tire spreading and rotating frame which includes a pneumatically operated lift for elevating a tire carcass to be inspected. Once the carcass is lifted into place on the frame, a pair of pneumatically operated actuated spreaders grip the top portions of the sidewall and spread the sidewalls apart. An x-ray source and an image intensifier are mounted so that, as the tire carcass is rotated, one of the sidewalls or the tread is selectively positioned between the x-ray source and the image intensifier. A video camera is optically coupled to the image intensifier and is connected to a live video monitor and to a video cassette recorder (VCR). As the tire is rotated, a fluoroscopic image of the tire is displayed on the monitor. The images of the tire are video recorded for later comparison with previously or subsequently generated images of the same tire taken during previous retreading operations or after it has been retreaded and placed back in service and during subsequent retreading operations. The frame, x-ray source, and image intensifier are placed in a shielded environment which is preferably mobile, such as a trailer, to protect the operator from exposure to x-rays. The x-ray source and image intensifier are mounted on an arm which is attached to a swivel base which is driven by a motor.

After the tire is positioned and spread, the x-ray source and image intensifier are positioned to examine a first sidewall. The tire carcass is then rotated 360 degrees about the central and horizontal axis thereof, so that the first sidewall is completely x-rayed. With the tire carcass remaining in place, the x-ray source and image intensifier are swung about a vertical axis by the motor so that x-ray equipment is then in position to x-ray the tread portion. The tire is then rotated 360 degrees and the x-ray source and the fluoroscope are then swung again to allow examination of the opposite sidewall and the process is repeated again. Once a tire carcass is positioned and the sidewalls spread for inspection, all of the remaining inspection steps can be controlled remotely so that an operator need not leave his protected environment until the tire carcass is completely inspected.

The invention includes means to synchronize the display of previously recorded images with currently or subsequently generated images of a tire. A radiopaque tag with a serial number is placed on the tire in a standardized location, such as adjacent the serial number of the tire, and the inspection is conducted during a full rotation of the tire from a point from which the tag is visible on the monitor until the tag is again visible. When a defect is detected on the monitor screen, a hard copy of the defect can be obtained by stopping the tire rotation and placing a sheet of x-ray sensitive film on the tire covering the area of the defect after which the film is exposed by activation of the x-ray source to provide a photographic record of the defect. The area of the defect may be marked, such as with chalk, to facilitate repair if repair is possible.

OBJECTS AND ADVANTAGES OF THE INVENTION

The principal objects of the present invention are: to provide an apparatus and method for inspection of tires using x-rays to discover and locate defects; to provide such an apparatus and method which are particularly well adapted for use in connection with inspecting tire carcasses prior to the retreading of tires; to provide such an apparatus including means for rotating a tire carcass about a central axis thereof while one section of the tire is positioned between an x-ray source and an x-ray image intensifier; to provide such an apparatus which is adapted to spread the sidewalls of the tire to better position the x-ray source for inspection; to provide such an apparatus in which the x-ray source and image intensifier are mounted on an arm which is attached to a swivel base which is rotatable about a vertical axis which is perpendicular to the central axis of the tire being examined so that both sidewalls and the tread can be examined without repositioning the tire; to provide such an apparatus which has a video camera for generating video signals representing images formed on the x-ray image intensifier; to provide such an apparatus which has a video monitor for displaying the video images and a video recorder for recording and playing back the video images; to provide such an apparatus which is portable or mobile, such as by mounting the apparatus in a trailer; to provide such an apparatus which is x-ray shielded to protect an operator; to provide a method of operating such an inspection apparatus including the playback of previously generated fluoroscopic images of a tire simultaneously with the current generation of fluoroscopic images of the same tire for comparison to detect new defects in the tire; to provide such an apparatus in which the x-ray source and x-ray image intensifier are remotely positionable relative to the tire to permit all walls of an entire tire to be inspected without requiring the operator to leave a protected environment; and to provide such an inspection apparatus and method which are economical to manufacture and produce, safe and effective, and which are particularly well adapted for their intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is an enlarged and fragmentary perspective view of a swivel mount and motor drive for an x-ray source and x-ray image intensifier for the tire inspection apparatus, with a protective frame shown partially broken away to illustrate a chain and sprocket drive.

FIG. 3 is a fragmentary end view of the tire inspection apparatus, showing the tire being spread by a pneumatically actuated tire spreader.

FIG. 4 is a fragmentary top plan view of the tire inspection apparatus showing the x-ray source and x-ray image intensifier in solid lines positioned for inspecting one sidewall, and twice in phantom lines for inspecting the tread and the opposite sidewall.

FIG. 5 is a fragmentary view of a tire with an x-ray sensitive film positioned thereon during irradiation to provide a permanent record of a detected defect.

DETAILED DESCRIPTION OF THE INVENTION

Figure 1:
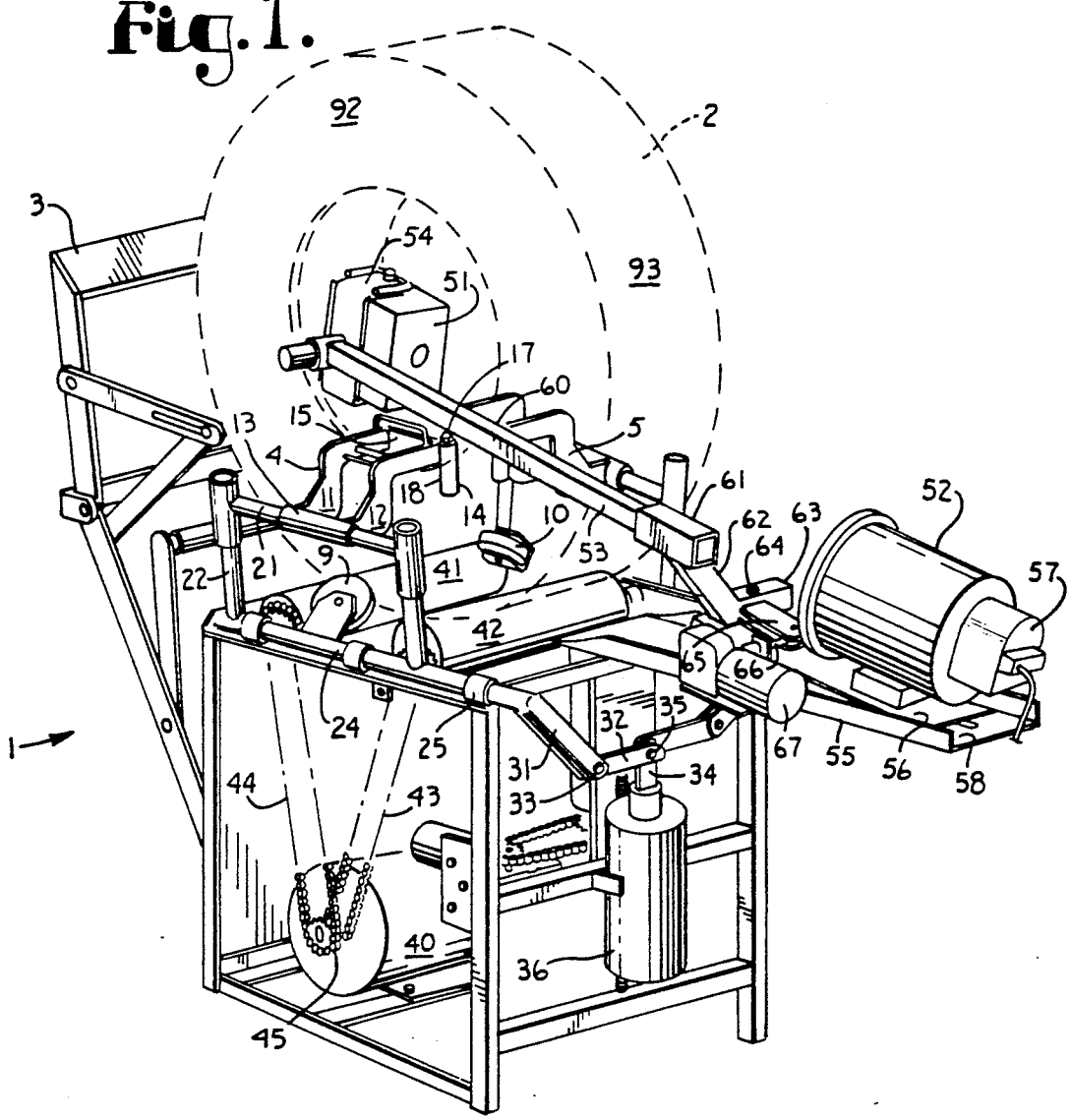
FIG. 1 is a perspective view of a tire inspection apparatus in accordance with the present invention, showing a tire to be inspected in phantom lines.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 refers generally to a tire inspection apparatus in accordance with the present invention. In FIG. 1, a tire 2 is shown in phantom lines mounted on the apparatus 1.

A pneumatically actuated lift 3 is used to elevate the tire 2 and set it in place on the apparatus 1. A pair of spreader arms 4 and 5 are inserted into the interior of the tire 2 to spread the tire sidewalls, as better illustrated in FIG. 3. The spreader arms 4 and 5 are mirror images of each other, and thus only the spreader arm 4 will be described in detail with the arm 5 being essentially identical except as a mirror image.

The spreader arm 4 comprises two somewhat L-shaped flat plate sections 11 and 12 which terminate in spreader teeth 14. The plates 11 and 12 are connected at one end by a cross member 15 and at the other end by a sleeve 13. A plurality of reinforcing rods 16 act to provide added rigidity to the spreader arm 4. The sleeve 13 has inserted therein a rod 21 which is connected at either end to a pair of upright supports 22 and 23, which are in turn connected to another rod 24 which is rotatable through a plurality of collar supports 25.

The rod 24 is rigidly connected to a connecting arm 31 which is rotatably connected to another arm 32 by a pin 33. The arm 32 is connected to a piston 34 by a pin 35. A pneumatic cylinder 36 is connected to the piston 34. A pair of angled supporting rollers 9 and 10 rotate as the tire 2 is rotated and act to support the tire 2 in an upright position. The operation of the spreaders 4 and 5 will now be explained.

Once the tire 2 is placed on the apparatus 1, an operator pushes a switch on a spreader control 120 (FIG. 6), which causes air to force the piston 34 upward within the pneumatic cylinder 36. This forces the arm 32 upward, causing the connecting arm 31 to rotate the rod 24 within the collars 25. This forces the upright supports 22 and 23 outward, which causes the spreading teeth 14 to be urged against and spread the sidewalls of the tire 2. Typically, the spreader arm 4 causes the sidewalls to separate from a normal separation of about 2 to 4 inches to a separation of between 9 and 11 inches. The spreading teeth 14 include a sleeve 18 which engages the inside of the inside sidewall of the tire 2. The sleeve 18 is adapted to rotate about a vertical pin 17 as the tire 2 is rotated about its central axis. The structure for supporting the tire 2 and producing such a rotation of the tire 2 will now be described.

When the tire 2 is positioned on the apparatus 1, it rests on a pair of rollers 41 and 42. Once the spreader teeth 14 have been operated to spread the tire, these rollers 41 and 42 are operable and are turned by a tire rotating motor 42. The motor 42 turns a sprocket 45 which drives a pair of chains 43 and 44. The chain 44 rotates the roller 41 through another sprocket 47 fixedly attached to the roller 41, while the chain 43 rotates the roller 42 through still another sprocket 48. The rollers 41 and 42, when rotated by the motor 42, cause the tire 2 to rotate about its central axis. The spreader teeth 14 and the angled rollers 9 and 10 hold the tire securely on the apparatus 1 as it is being rotated.

The tire inspection apparatus 1 includes an x-ray source 51 and a fluoroscopic device or x-ray image intensifier 52 which are connected to opposite ends of an arm 53. The x-ray source 51 is rigidly clamped to the arm 53 by a clamp 54 while the x-ray image intensifier 52 is securely mounted on a slidable carriage 56. The arm 53 is secured to the carriage 56 mounted in a channel 58 in a platform 55. The carriage 56 is elevated at the tire end 59 thereof by feet or posts (not seen). The arm 53 includes an elongate section 60 connected by a sleeve 61, allowing slidable adjustment therebetween, to an offset section 62. The offset section includes a pivot arm 63 centrally and pivotally connected to the carriage 56 by a pivot pin 64.

A pair of parallel and spaced pivot plates 65 are secured to the pivot arm 63 and project perpendicularly from the pivot pin 64. Captured between the distal ends of the pivot plates 65 is a jock screw and nut assembly 66 that, in turn, is operably connected to a fine positioning motor means such as motor and gearbox assembly 67. In this manner, the motor and gear box assembly 67 allows fine control of the angular positioning of the arm 53 to image specific regions of the tire 2, such as parallel to the sidewall to detect separation of internal layers.

Referring to FIG. 2, again, the carriage 56 is slidable relative to the platform 55 so that the apparatus 1 can be adjusted to accommodate tires of various sizes and remains in a selected position until manual effort is again applied to move the carriage 56 relative to the platform 55. If a more secure placement is desired, it is foreseen that a channel may be cut in the platform 55 and a set screw inserted through the carriage 56 and the platform 55 and tightened to hold the carriage 56 in place.

The platform 55 is attached to a vertical post 74 by a plurality of through-bolts 76. The post 74 is housed within a protective shield 75, shown partially cut away in FIG. 2. The post 74 is mounted to be rotatable about its central axis and terminates in a sprocket 81, to which is attached a chain drive 82. The chain 82 is also attached to a motor sprocket 83 which is rotated by swing motor means such as motor 84 via gear box 85. The motor 84 is programmable in that a plurality of positions can be preprogrammed and the motor will operate until it reaches each one of the preprogrammed positions and then automatically shut off until reactivated at which time, it moves to the next position.

FIG. 3 illustrates a tire 2 positioned on the apparatus 1 with its sidewalls spread by spreader arms 4 and 5 and the x-ray source 51 and the x-ray image intensifier 52 positioned to examine one sidewall 91. The tire 2 is rotated by the rollers 41 and 42 (FIG. 1) while the x-ray source 51 emits x-rays which pass through the sidewall 91 and are received by the x-ray image intensifier 52. A video camera 57 is optically coupled to the x-ray image intensifier 52 and generates video signals representing the fluoroscopic images formed on the x-ray image intensifier 52. The video camera 57 is connected to a video recorder/playback unit 104 (FIG. 6) such as a video cassette recorder (VCR) unit, to record the fluoroscopic images generated from each tire 2 for later study or for comparison with earlier generated images of the tire 2. The camera 57 has a live video monitor 102 connected thereto for displaying live images while the VCR 104 has a recorder video monitor 106 coupled thereto to display recorded images. An image printer 121 can also be connected to the camera 57 to provide a hard copy record of the radiographic image of the tire 2. Additionally, a character generator 105 is connected to the camera 57, the VCR 104 and the image printer 121 to enable alphanumeric information such as dates, times, serial number of the tire, etc. to be recorded as well.

The operation of the motor 84 and the rotating platform 55 will now be described especially with reference to FIG. 4. FIG. 4 illustrates 3 different positions of the platform 55, one in solid lines and the other two in phantom lines. Once a tire 2 is positioned for inspection, as shown in FIG. 3, the x-ray source 51 and the x-ray image intensifier 52 are positioned as shown in FIG. 3 to examine the sidewall 91. Once the tire 2 is completely rotated through one revolution, the motor 84 is started, swinging the support 55 to a central position, as shown in phantom in FIG. 4, and the tire 2 is again rotated through another complete revolution, so that the tire tread 93 can be completely examined. Upon completing this revolution, the motor 84 is again started, swinging the platform 55 to the third illustrated position so that the opposite sidewall 92 can be examined. The motor 84, as well as the spreader cylinder 36, the tire rotating motor 42, the fine positioning motor assembly 67, the x-ray source 51, the x-ray image intensifier 52, and the video camera 57 are remotely controllable so that an operator need not leave his protected environment until the tire 2 has been completely x-rayed for defects.

The x-ray source 51 is a conventional x-ray tube such as is used in other industrial x-ray applications. The x-ray source 51 is connected to an x-ray source time/control circuit 101 (FIG. 6) which includes a high voltage supply providing power in the range of 70 to 75 kilovolts at about three milliamperes. The x-ray source 51 is operated continuously during an inspection cycle such that positive cooling of the source 51 is advisable to extend its useful life. As will be detailed below, when a tire defect is observed on the screen of the live monitor 102, an x-ray film at the site is typically exposed to show a repairer where to find the defect. During such exposure, the x-ray source timer/control 101 is adjusted to control the time of exposure.

Figure 8:
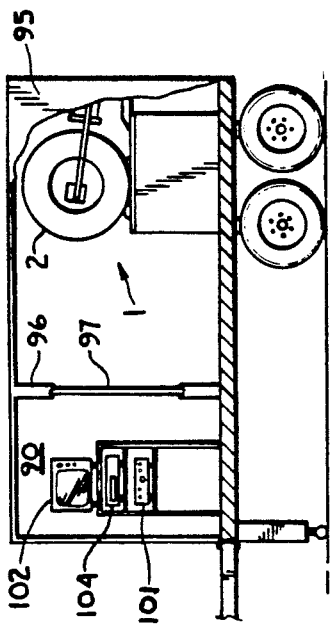
FIG. 8 is a side elevational view at a reduced scale of a shielded trailer with a portion of a wall shown broken away to illustrate the tire x-ray apparatus therein.

The x-ray image intensifier 52 includes a screen (not shown) coated with phosphors which are illuminated proportionate to the intensity of x-rays incident on the screen. The x-ray image intensifier 52 includes fluoroscope control circuitry 103 to provide power thereto and to allow control of, for example, the sensitivity and brightness and, to some extent, the contrast of the x-ray image intensifier 52. The video camera 57 is mounted on the x-ray image intensifier 52 and is optically coupled in such a manner that the image formed on the fluoroscope screen is scanned by the camera 57 and is converted to a video signal. The camera 57 is connected to the live video monitor 102 and the VCR 104 such that the fluoroscopic image of the tire 2 is displayed on the monitor 102 and recorded on the VCR 104. The apparatus 1 is preferably portable and, in the illustrated embodiment, is housed in a trailer 94 (FIG. 8). The trailer 94 may be any suitable vehicle, such as a mobile home type vehicle or, as illustrated, truck type trailer. The trailer 94 has x-ray shielded external walls 95 to prevent the leakage of x-rays external to the trailer 94. The external walls 95 may be shielded as by the incorporation of lead panels or plates (not shown) therein. In order to prevent overexposure of an operator of the apparatus 1 by x-rays, an operator compartment or room 90 is formed within the trailer 94 as by an x-ray shielded wall 96 between the operator's compartment 90 and the remainder of the trailer 94 having the apparatus 1 therein. The wall 96 has lead panels or plates (not shown) or other shielding material incorporated therein. The wall 96 is provided with a leaded window 97 to allow the operator to view the apparatus 1 during operation without risking exposure by x-rays.

In operation, a tire 2 not mounted on a wheel is rolled into the trailer 94 and is loaded by the lift 3 onto the rollers 41 and 42 of the tire inspection apparatus 1. A radiopaque index tag 50, preferably having a serial number marked thereon or stenciled therein, is placed on the tread 93 of the tire 2 in a standardized location to identify the tire and to signal the beginning and the end of an inspection rotation cycle. The serial number on the tag 50 is visible on the live video monitor 102 during irradiation. A standardized location on the tire 2 may be, for example, in alignment with a manufacture's serial number imprinted on the sidewall 91 of the tire 2, or the like. The sidewalls 91 and 92 are held open by the pneumatically operated spreader arms 4 and 5, as described earlier.

As illustrated in FIGS. 1 and 3, the x-ray source 51 and x-ray image intensifier 52 are positioned in alignment to irradiate an area approximately the width of the tread 93 or the sidewall 91 of the tire 2 as it is rotated about its central axis with the tire 2 positioned between the x-ray source 51 and the x-ray image intensifier 52. As shown, particularly in FIG. 1, the x-ray source 51 and the x-ray image intensifier 52 are spaced apart approximately the length of the outer diameter of the tire 2. Placement at this distance causes "softer" x-rays to expose the x-ray image intensifier 52 for a given operating voltage resulting in an image having greater contrast. The reason for this is that the softer rays are less penetrating to the materials of the tire 2 whereby there is a greater difference in absorption of the x-rays by the different materials and thicknesses thereof. Thus, more tire structure detail is visible. This distance can be made adjustable to allow the radiation pattern to be widened or narrowed as desired.

When the tire 2 has been properly positioned and prepared, the x-ray image intensifier 52 is activated through the fluoroscope control 103, and the video camera 57 and the live video monitor 102 are activated. Initially, the tire 2 may be irradiated and inspected by viewing the live monitor 102 to discover and locate any defects in the tire 2, such as previously undiscovered punctures or broken or distorted cords. Damaged reinforcing wires or cords that have been broken due to underpressurization of the tire or the like are one of the most important defects to find since such are not possible to repair and indicate that the carcass should be discarded prior to relatively expensive retreading. For this, the motor 40 is activated by a motor control 108, thereby rotating the tire between the x-ray source 51 and the x-ray image intensifier 52. The x-ray source 51 is activated to irradiate the x-ray image intensifier 52 through the tire 2, and a fluoroscopic image is formed on the x-ray image intensifier 52 which is scanned by the camera 57 and converted to a video signal. The video signal is reconverted to an image by the live video monitor 102 which may be viewed by the operator as the tire is rotated. If an irregularity is detected, the motor 40 is deactivated and may be reversed to hold the irregularity on the screen of the monitor 102 for a closer inspection.

If, through the experience of the operator, the irregularity appears to be a defect or damage, a "hard" copy of the x-ray image may be made. For this purpose, the x-ray source 51 is deactivated, and the operator leaves the shielded compartment 90 and attaches an x-ray sensitive film pack 111 (FIG. 5) on the tire 2 in the area covered by the x-ray image intensifier 52. The film pack 111 may consist of a piece of x-ray sensitive film 112 in a light impervious envelope (not shown) with an adhesive applied thereto. Alternatively, strips of an adhesive tape 113 may be provided on the film pack 111. At the same time, the area of the defect is preferably marked, as with chalk, so that the defect can be subsequently found and repaired, if necessary or possible. The operator reenters the compartment 90 and causes a timed x-ray exposure of the film 112 through the defect to occur by operation of the x-ray timer/control 101. The x-ray film 112 will be developed later to provide documentation of the defect. X-ray films generally provide much higher resolution detail than either fluoroscopic images or video images created therefrom. The operator may also cause a video image to be printed by activation of an image printer 121. The image printer 121 may, for example, be a device such as a model UP-811 or UP-701 video graphic printer manufactured by Sony Medical Products Company of Hackensack, N.J. Alternatively, other types of hard copy imaging devices may be employed.

After both sidewalls 91 and 92 and the tread 93 have been completely inspected as described above, all of the detected irregularities are studied and documented and, if appropriate, the fluoroscopic images of the tire 2 are video recorded. A video cassette (not shown) is placed in the video cassette recorder (VCR) 104, and the tire 2 is rotated such that the index tag 50 is aligned between the x-ray source 51 and the x-ray image intensifier 52. The operator then enters the compartment 90 and activates the x-ray source 51, the x-ray image intensifier 52, the VCR 104 by means of a VCR control unit 109, and the motor 40. The rotation and irradiation of the tire 2 is continued at least until the radiation tag 50 reappears on the screen of the live video monitor 102, at which time the operation may be terminated. The video recording thus produced may be used for later comparison with a live generation of fluoroscopic images of the same tire 2. During the display of images on the monitor 102, and during the recording of images by the VCR 104, the character generator 105 is preferably activated to display identifying alphanumeric information on the images. The character generator 105 may be similar to that used in association with the AFP Satellite 810 series of video imaging devices which are manufactured by the AFP Imaging Corporation of Elmsford, N.Y.

After inspection, the tire 2, if new, is mounted on a truck and placed into service. If the tire 2 is not new, but is of adequate quality, it is retreaded and placed into service. Otherwise, if the carcass of the tire 2 is too badly damaged for safe retreading, it is disposed of in an appropriate manner. After the tread 93 of the tire 2 is worn down by use on the road, and before retreading again, it is once more inspected in the manner described above. As the tire 2 is reinspected, previously generated fluoroscopic images of the tire 2 are replayed on the VCR 104 and viewed on the recorder video monitor 106 as current images of the tire 2 are generated and displayed on the live video monitor 102. As the sets of images are played on the monitors 102 and 106, preferably in substantial synchronism for comparison of corresponding sectors of the tire 2, the differences in the images facilitate the discovery of any new irregularities or defects in the tire 2 from use on the road.

Figure 6:
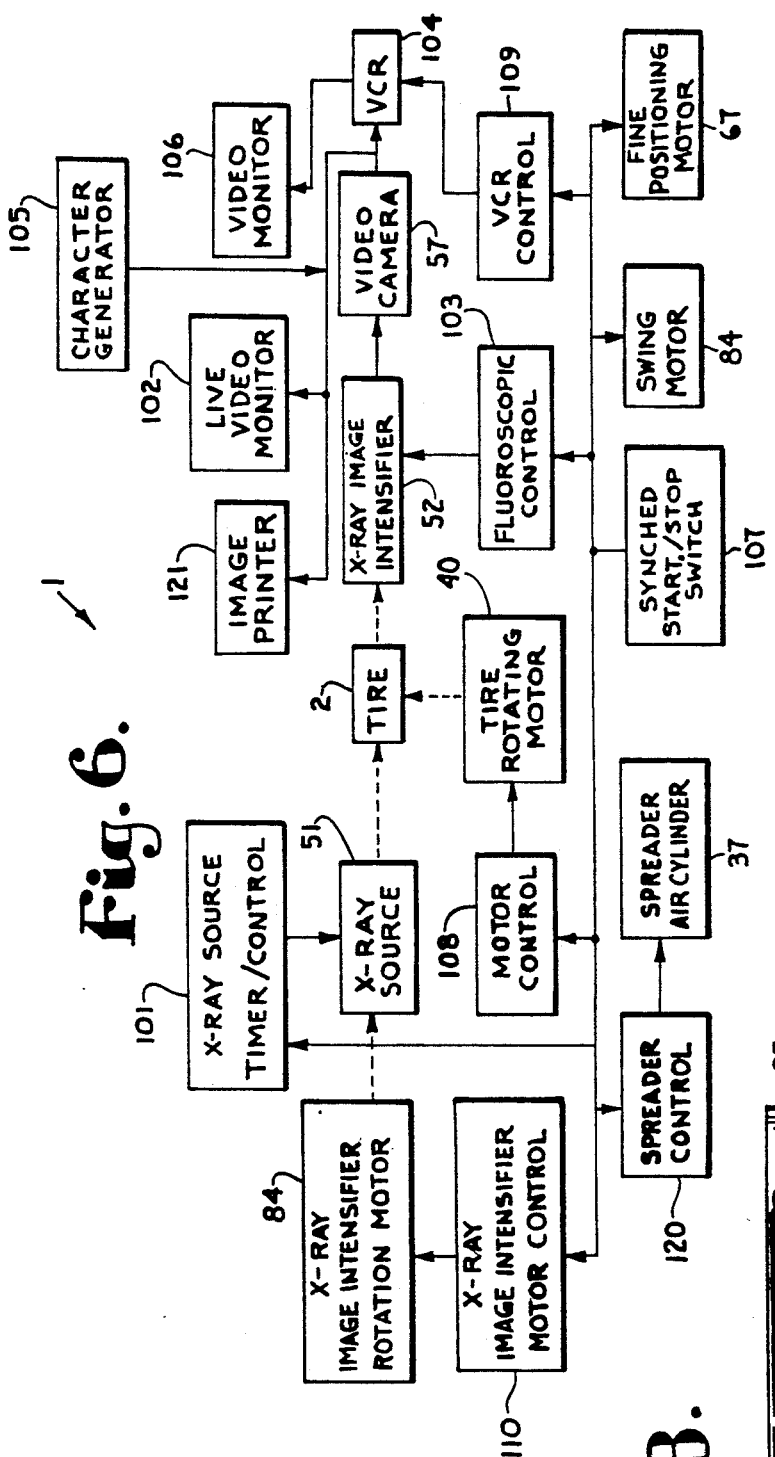
FIG. 6 is a general block diagram illustrating components of the tire inspection apparatus in accordance with the present invention, and illustrating a synchronized start/stop switch for synchronizing the playback of a previously recorded image of a tire with a live image of the same tire.

FIG. 6 illustrates a block diagram of the inspection apparatus 1, including a synched start/stop switch 107. The switch 107 is connected to the x-ray source timer/control 101, the motor control 108, the fluoroscope control 103, the VCR control 109, and the x-ray/fluoroscope motor control 110. In operation of the system, the tire 2 is rotated to locate the index tag 50 in alignment between the x-ray source 51 and the x-ray image intensifier 52, and the VCR 104 is operated by use of the VCR control 109 to position the tape at a position displaying the index tag 50 on the video monitor 106.

Upon operation of the switch 107, the x-ray source 51, the tire rotation motor 40, the x-ray image intensifier 52, and the VCR 104 are all operated simultaneously. By this means, the previously recorded fluoroscopic images are played back simultaneously with the generation of current images of the tire 2. The motor 40 is operated at a relatively slow speed so that it takes approximately one and a half minutes for a complete rotation of the tire. The x-ray/fluoroscope motor control 110 is operated in synchronism with the rotation of the tire 2 so that all three inspection positions of the x-ray/fluoroscope platform 55 are examined in turn. With the relatively slow rotation speed, there is no need for exact synchronism since it is only necessary for the sets of images to be comparatively viewed at corresponding sectors of the tire 2.

Figure 7:
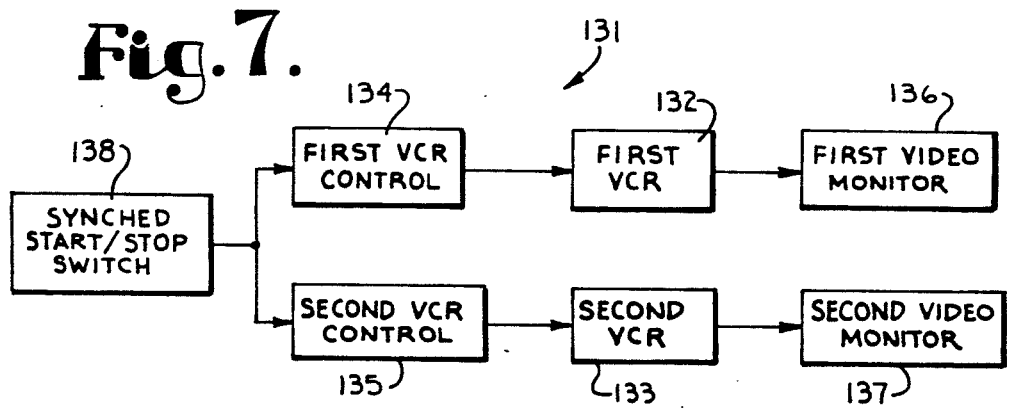
FIG. 7 is block diagram of some components of the tire inspection apparatus and illustrating a synchronized start/stop switch for synchronizing the playback of two previously recorded images of a tire.

FIG. 7 illustrates an alternative synchronized tire viewing system 131 for simultaneous viewing of two sets of recorded fluoroscopic images of the tire 2. The system 131 employs 2 VCR's 132 and 133 controlled by respective VCR controls 134 and 135 and displaying images on respective video monitors 136 and 137. A synchronized start/stop switch 138 is connected to the first and second VCR controls 134 and 135 and activates them simultaneously. In the system 131, the sets of the images of the tire 2 are recorded as described above on separate tape cassettes for simultaneous playback on the VCR's 132 and 133. For simultaneous playback, each of the VCR's 132 and 133 is operated by its respective control 134 and 135 to position the tapes at positions which display the starting image of the tag 50. Then, the switch 138 is operated to activate the playback mode of both of the VCR's 132 and 133 simultaneously.

It is to be understood that while certain forms of the present invention have been illustrated and described herein, it is not to be limited to the specific forms or arrangement of parts described and shown.

What is claimed and desired to be secured by Letters Patent is as follows:

1. In a tire inspecting apparatus including means for rotating the tire about a central axis during inspection, an x-ray source for generating x-rays to pass through selected sections of the tire and an x-ray image intensifier positioned opposite the x-ray source for receiving the x-rays after the x-rays have passed through said sections of said tire and generating a fluoroscopic image therefrom; the improvement comprising:

(a) tire spreader means including a pair of spreader teeth adapted to spread the sidewalls of said tire for inspection while said tire is rotated about said central axis, whereby the path of the x-rays from said x-ray source can be positioned within the spread sidewalls to irradiate only one sidewall or only the tread at a particular time; each of said teeth extending radially along an inner wall of a respective sidewall when in a sidewall spreading position thereof; each of said teeth including an outer sleeve that is aligned to rotate with a radial axis of a respective tooth; said spreading means including structure means to selectively pivot said teeth between said sidewall spreading position and a spaced position from said sidewalls.

2. A tire inspecting apparatus according to claim 1, wherein:

(a) said spreader means is pneumatically actuated.

3. A tire inspection apparatus comprising:

(a) a support frame for supporting a tire to be inspected, said support frame including a base adapted to be supported by a floor and a plurality of upright legs supporting a plurality of horizontal support members;

(b) a plurality of rollers positioned between two of said horizontal support members, said rollers spaced apart a sufficient distance to provide positive support for a tire to be inspected;

(c) a first motor connected to said rollers by first drive means, said first motor and said rollers adapted to rotate said tire about a central axis of the tire;

(d) an a-ray source and an x-ray image intensifier mounted at opposite ends of an arm, said x-ray source generating x-rays which penetrate said tire and which create a fluoroscopic image of a portion of said tire, including any defects therein, on said x-ray image intensifier, said arm being attached to a carriage, (e) a platform connected to an upright post, said platform adapted to receive said carriage, said carriage and said platform being adjustable relative to each other, said upright post being rotatable about a vertical axis and being connected to a second motor by second drive means, whereby said second motor rotates said arm about said vertical axis; and (f) fluid operated spreader means including a pair of spreader arms mounted on said frame, said spreader arms adapted to spread apart the sidewalls of said tire so that a path of x-rays of said x-ray source can be positioned inside the sidewalls of said tire and including rotating means to allow said tire to be rotated while said sidewalls are spread apart, whereby; each of said spreader arms including at least one tooth extending radially along an inner wall of a respective sidewall when in a sidewall spreading position thereof; each of said teeth including an outer sleeve that is aligned and rotatable with a radial axis of a respective tooth; said spreading means including structure means to selectively pivot said teeth between said sidewall spreading position and a spaced position from said sidewalls.

4. A tire inspection apparatus in accordance with claim 3, and further comprising:

(a) a video camera optically coupled to said x-ray image intensifier to create video images from the fluoroscopic images on said x-ray image intensifier; and (b) a live video monitor and a VCR connected to said video camera to display and record, respectively, the video images from said video camera.

5. A tire inspection apparatus in accordance with claim 4, wherein;

(a) said first and second motors, said x-ray source, said x-ray image intensifier and said video camera are remotely controllable from a protected compartment so that the entire tire can be examined by an operator without leaving the protected compartment. 9. A tire inspection apparatus in accordance with claim 8, and further comprising: (a) a video camera optically coupled to said x-ray image intensifier to create video images from the fluoroscopic images on said x-ray image intensifier; and (b) a live video monitor and a VCR connected to said video camera to display and record, respectively, the video images from said video camera. A tire inspection apparatus in accordance with claim 9, wherein; (a) said first and second motors, said x-ray source, said x-ray image intensifier and said video camera are remotely controllable from a protected compartment so that the entire tire can be examined by an operator without leaving the protected compartment.

* * * * *